United States Patent
Tai et al.

(10) Patent No.: US 10,617,011 B2
(45) Date of Patent: Apr. 7, 2020

(54) MICRO-FABRICATED GROUP ELECTROPLATING TECHNIQUE

(71) Applicant: California Institute of Technology, Pasadena, CA (US)

(72) Inventors: Yu-Chong Tai, Pasadena, CA (US); Han-Chieh Chang, Pasadena, CA (US); Xiaoxiao Zhang, Los Angeles, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 120 days.

(21) Appl. No.: 14/974,404

(22) Filed: Dec. 18, 2015

(65) Prior Publication Data
US 2016/0105973 A1   Apr. 14, 2016

Related U.S. Application Data

(63) Continuation of application No. PCT/US2014/055474, filed on Sep. 12, 2014.
(Continued)

(51) Int. Cl.
*C25D 1/04* (2006.01)
*H05K 3/24* (2006.01)
(Continued)

(52) U.S. Cl.
CPC .......... *H05K 3/242* (2013.01); *A61N 1/0543* (2013.01); *C23C 14/14* (2013.01); *C23C 14/24* (2013.01);
(Continued)

(58) Field of Classification Search
None
See application file for complete search history.

(56) References Cited

U.S. PATENT DOCUMENTS 3,484,341 A  * 12/1969  Devitt ................. H01L 21/2885
                                                              148/DIG. 20
4,496,432 A  *  1/1985  Nauman ................. C25D 11/00
                                                              204/400
(Continued)

FOREIGN PATENT DOCUMENTS

CN          1473206         2/2004
CN          1649473         8/2005
(Continued)

OTHER PUBLICATIONS

Watanabe T., et al., "Evaluation of Platinum-Black Stimulus Electrode Array for Electrical Stimulation of Retinal Cells in Retinal Prosthesis System", Japanese Journal of Applied Physics, 2007, 46, p. 2785 (Year: 2007).*
(Continued)

*Primary Examiner* — Stefanie S Wittenberg
(74) *Attorney, Agent, or Firm* — Kilpatrick Townsend & Stockton LLP

(57) ABSTRACT

Methods, and devices produced by the methods, for electroplating a multitude of micro-scale electrodes that are electrically isolated from each other on a cable or other device is described. A localized area of connections on another end of the cable is shorted together by depositing a metal sheet or other conductive material over the localized area. The metal sheet is connected to a terminal of a power supply, and the electrode end of the cable is immersed in an electrolyte solution for electrodeposition by electroplating. After the electrodes are electroplated, the metal sheet is removed from the cable in order to re-isolate the electrodes.

20 Claims, 10 Drawing Sheets

Related U.S. Application Data

(60) Provisional application No. 61/878,992, filed on Sep. 17, 2013.

(51) Int. Cl.

| | | |
|---|---|---|
| *A61N 1/05* | (2006.01) | |
| *C23C 14/14* | (2006.01) | |
| *C23C 14/24* | (2006.01) | |
| *H05K 3/06* | (2006.01) | |
| *H05K 3/40* | (2006.01) | |
| *H05K 3/28* | (2006.01) | |
| *H05K 3/32* | (2006.01) | |
| *H05K 1/18* | (2006.01) | |

(52) U.S. Cl.
CPC ............... *C25D 1/04* (2013.01); *H05K 3/064* (2013.01); *H05K 1/189* (2013.01); *H05K 3/244* (2013.01); *H05K 3/28* (2013.01); *H05K 3/321* (2013.01); *H05K 3/4007* (2013.01); *H05K 2203/0191* (2013.01); *H05K 2203/0361* (2013.01); *H05K 2203/0723* (2013.01); *H05K 2203/1338* (2013.01)

(56) References Cited

U.S. PATENT DOCUMENTS

| | | | | |
|---|---|---|---|---|
| 4,512,854 | A * | 4/1985 | Grah | C25D 5/022 204/279 |
| 5,109,844 | A | 5/1992 | De Juan et al. | |
| 5,413,962 | A * | 5/1995 | Lur | H01L 21/7682 148/DIG. 73 |
| 7,846,285 | B2 * | 12/2010 | Zhou | C25D 3/62 156/150 |
| 7,877,866 | B1 | 2/2011 | Greenberg et al. | |
| 8,000,804 | B1 | 8/2011 | Wessendorf et al. | |
| 2003/0233133 | A1 | 12/2003 | Greenberg et al. | |
| 2007/0071886 | A1 | 3/2007 | Babb et al. | |
| 2007/0120235 | A1 * | 5/2007 | Shimoishizaka | H01L 23/4985 257/668 |
| 2008/0288036 | A1 | 11/2008 | Greenberg et al. | |
| 2008/0319493 | A1 | 12/2008 | Zhou et al. | |
| 2009/0124965 | A1 * | 5/2009 | Greenberg | A61N 1/0531 604/67 |
| 2010/0044860 | A1 | 2/2010 | Haba et al. | |

FOREIGN PATENT DOCUMENTS

| | | |
|---|---|---|
| CN | 102197478 | 9/2011 |
| CN | 105432156 | 3/2016 |
| EP | 0 110 114 A1 | 6/1984 |
| EP | 1 289 352 A2 | 3/2003 |
| EP | 2 280 592 A1 | 2/2011 |

OTHER PUBLICATIONS

International Application No. PCT/US2014/55474, International Search Report and Written Opinion dated Sep. 12, 2014, 14 pages.
EP14845731.0 , "Extended European Search Report", dated Aug. 23, 2017, 7 pages.
Chen et al., "A 37.6mm$^2$ 1024-Channel High-Compliance-Voltage SoC for Epiretinal Prostheses," ISSCC Biomedical Circuits & Systems, Session 16, Feb. 19, 2013, 3 pages, IEEE International Solid-State Circuits Conference.
Chen et al., "Analysis and Design of Data Transmission Protocol for 1024-channel Retinal Prosthesis," 33rd Annual International Conference of the IEEE, Aug. 30-Sep. 3, 2011, pp. 4010-4013, Boston, Massachusetts.
Humayun et al., "Visual Perception in a Blind Subject with a Chronic Microelectronic Retinal Prosthesis," Vision Research, Nov. 2003, pp. 2573-2581, vol. 43, No. 24.
Negi et al., "In Vitro Comparison of Sputtered Iridium Oxide and Platinum-Coated Neural Implantable Microelectrode Arrays," Biomed. Mater., Feb. 2010, 9 pages, vol. 5, No. 1, IOP Publishing, United Kingdom.
Randles, "Kinetics of Rapid Electrode Reactions," Discuss. Faraday Soc., Jan. 1, 1947, pp. 11-19, vol. 1.
Shah et al., "Electrical Properties of Retinal—Electrode Interface," J. Neural Eng., Feb. 2007, pp. S24-S29, vol. 4, No. 1, IOP Publishing Ltd, United Kingdom.
CN201480041315.9 , "Office Action", dated Sep. 18, 2017, 6 pages.
CN201480041315.9 , "Notice of Decision to Grant", dated Jun. 1, 2018, 3 pages.

\* cited by examiner

MICRO-FABRICATED GROUP ELECTROPLATING TECHNIQUE

CROSS-REFERENCES TO RELATED APPLICATIONS

This application is a (bypass) continuation of International Application No. PCT/US2014/055474, filed Sep. 12, 2014, which claims the benefit of U.S. Provisional Patent Application No. 61/878,992, filed Sep. 17, 2013, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under EEC0310723 awarded by the National Science Foundation. The government has certain rights in the invention.

BACKGROUND

1. Field of the Art

Embodiments of the present invention generally relate to manufacturing surgically implanted electronics, in particular, an electrode array that connects with tissues, such as the retina of an eye.

2. Description of the Related Art

Age-related macular degeneration (AMD) and retinitis pigmentosa (RP) are two most common outer-retina degenerative diseases of the human eye. There is promise in the use of retinal prostheses in order to allow people afflicted with the diseases to see. Retinal prostheses, which bypass the defective outer-retina photoreceptors and electrically stimulate the inner-retina neurons directly, have allowed some blind people with AMD and RP to perceive light.

It is recognized that these early prostheses only involve a very small number of stimulating electrodes on the neurons. To realize facial recognition or large-sized letter reading, next-generation retinal prosthetic devices may use 1024 or more stimulating electrodes. A 1024-electrode implant can be configured as a 32-by-32 square array of electrodes or with different numbers of electrodes in rectangular, circular, or other shapes.

Due to surgical incision limitations on eyeballs, and to match the size of the macula lutea, the 1024 stimulating electrodes should be arranged on a small area within 7 millimeters (mm)×7 mm of one another. Therefore, each electrode should be small enough to fit in the allotted area and give an acceptable spatial resolution. However, smaller electrodes, because they are small, suffer from high impedance. High impedance leads to high charge densities, which may result in damage to tissue.

There is a need in the art for improved biocompatible electrodes and manufacturing techniques.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

BRIEF SUMMARY

Generally, an electroplating technique is described that is scalable to hundreds, thousands, or more individual electrodes that are electrically isolated from one another but connected by a cable or other device to a surface mount area for an integrated circuit (IC) chip. A continuous sheet of metal or other electrically conductive material can be deposited, by chemical vapor deposition (CVD) or otherwise, onto the surface mount area, effectively connecting all of conductive pads of the surface mount area together. Because all of the conductive pads of the surface mount area are electrically connected together, so are the electrodes at the other end of the cable. The metal sheet is then connected by a single connection point to the electroplating voltage supply while the other cable end with the electrodes is immersed in electrolyte solution for electroplating. After electroplating is complete, the metal sheet is removed by etching, peeling, or other means to again electrically isolate the electrodes.

Electroplating the electrodes with platinum black (Pt black) has been found to decrease impedance of each electrode by creating a rough surface and increasing surface area connected with body tissues. Biocompatible ribbon cable apparatuses created with the fabrication method are also described, which can be connected with IC chips and implanted within the body.

Some embodiments of the present invention are related to a method of electroplating numerous electrodes on a ribbon (or other) cable. The method includes providing a ribbon cable having a first end with a plurality of conductive pads arranged in a surface mount array, each conductive pad individually connected by an electrical conductor through the ribbon cable to a respective electrode at a second end of the ribbon cable, depositing a continuous sheet of conductive material over the surface mount array such that the conductive pads are electrically shorted with one another, immersing the electrodes at the second end of the ribbon cable in an electrolyte solution, connecting a power supply to the sheet of conductive material at the first end, thereby contemporaneously connecting the power supply to the electrodes at the second end, electroplating the electrodes using the power supply and the electrolyte solution, and removing the continuous sheet of conductive material from the surface mount array to electrically isolate the conductive pads from one another.

The conductive pads in the surface mount array can be each less than 100 microns (μm) in width and less than 100 μm from one another. The ribbon cable may consist entirely of biocompatible materials suitable for implantation into a mammal. The electroplating can include electroplating the electrodes with platinum black. The depositing can include thermal evaporation or chemical vapor deposition. The method can include depositing the continuous sheet of conductive material over the first end of the ribbon cable such that the continuous sheet of conductive material is larger than the surface mount array, applying photoresist to the first end of the ribbon cable, exposing a photomask to the first end of the cable, and removing excess conductive material to leave the continuous sheet of conductive material over the surface mount array. The depositing can include adhering an electrically conductive tape to the surface mount array. The removing can include peeling the continuous sheet from the surface mount array. The continuous sheet can include a material selected from the group consisting of aluminum, gold, platinum, silver, and titanium. The electroplating can include electroplating the electrodes with a metal selected from the group consisting of pure platinum, gold, and iridium. The surface mount array can be square or rectangular, and it can be planar. The surface mount array can have a fixed pitch between conductive pads. Microfabricating the ribbon cable can use photoresist, a photomask, etching, and chemical vapor deposition. The method can further include mounting an integrated circuit (IC) chip or IC socket to the surface mount array of the ribbon cable. The IC chip can include a plurality of metal pads in a two-dimensional array on a bottom of the IC chip, each metal pad of the IC chip connected to the surface mount array of the ribbon cable by conductive epoxy.

Some embodiments are directed to a method of electroplating numerous electrodes on a ribbon (or other) cable. The method includes providing a ribbon cable having a first end with a plurality of conductive pads suitable for connecting with one or more electrical components, each conductive pad individually connected by an electrical conductor to a respective lead in a localized tap area and through the ribbon cable to a respective electrode at a second end of the ribbon cable, depositing a continuous sheet of conductive material over the localized tap area such that the leads are electrically shorted with one another, immersing the electrodes at the second end of the ribbon cable in an electrolyte solution, connecting a power supply to the sheet of conductive material, thereby contemporaneously connecting the power supply to the electrodes at the second end, electroplating the electrodes using the power supply and the electrolyte solution, and removing the continuous sheet of conductive material from the localized tap area to electrically isolate the leads from one another.

Some embodiments are related to a biocompatible ribbon cable apparatus. The apparatus includes a biocompatible ribbon cable having a first end with a plurality of conductive pads arranged in a surface mount array, each conductive pad individually connected by an electrical conductor through the ribbon cable to a respective electrode at a second end of the ribbon cable, and a platinum black (Pt black) plating over each electrode, the plating increasing surface area of the electrode over a respective un-plated electrode.

The conductive pads in the surface mount array can be each less than 100 µm in width and less than 100 µm from one another. The ribbon cable electrodes can be operatively connected with retinal ganglion cells within an eyeball.

A further understanding of the nature and the advantages of the embodiments disclosed and suggested herein may be realized by reference to the remaining portions of the specification and the attached drawings.

Figure 1:
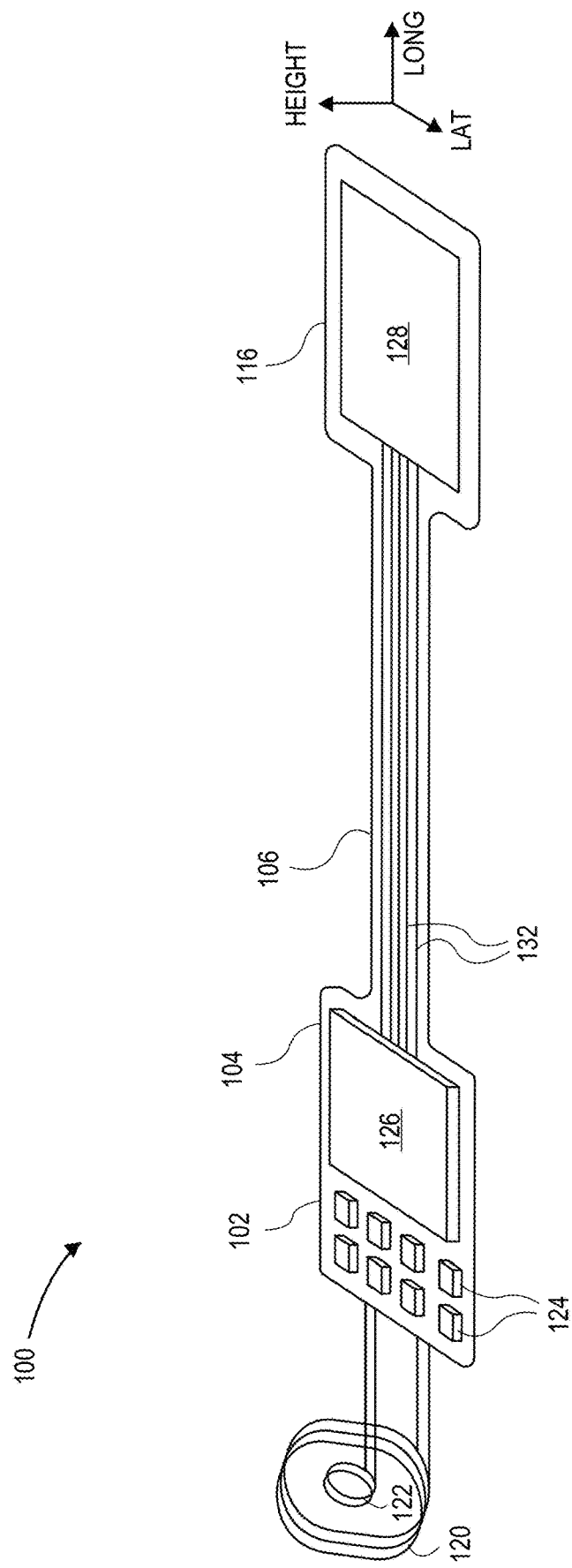
FIG. 1 is a perspective illustration of a ribbon cable in accordance with an embodiment.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Aspects are generally described regarding group electroplating technique with platinum black (Pt-black) or other plating substances to modify the surface of a multi-electrode array, which can be used on next-generation 1024-pixel retinal implants. This method is not only time efficient but also process friendly.

A large number of isolated electrodes on one end of a cable can be electroplated by adhering, sputtering, thermally evaporating onto, or otherwise depositing a sheet of metal over another end of a cable where an IC or other components will sit to connect with the electrodes. The metal sheet is used as a common contact point for an electroplating power supply. Meanwhile, the other end of the cable with the electrodes is submerged in an electrolyte as a cathode (or anode). The metal or other conductive substance to be plated is submerged in the electrolyte as an anode (or cathode). After the electrodes are electroplated, the metal sheet is peeled, dissolved, or otherwise removed from the contacts where the IC will sit, and the IC (or other components) are then connected.

Technical advantages of aspects of the invention are that a large number of electrically isolated electrodes can be quickly and efficiently plated all at once without having to manually make an electrical connection to each electrode. The resulting electroplating can increase surface roughness of each electrode, increasing surface area in contact with tissue in biological subjects, decrease impedance, and increase capacitance. The electroplating can make the electrodes last longer as well in the corrosive body fluids of a mammal, such as a human being.

FIG. 1 is a perspective illustration of a nearly-finished ribbon cable in accordance with an embodiment. System 100 includes ribbon cable 102, which has a portion 104 on which IC chip 126 is connected. Capacitors 124, power coil 120, and data coil 122 are connected to IC chip 126 by electrical traces 132 embedded in ribbon cable 102.

Electrical conductor traces 132 travel from ribbon cable portion 104 through central portion 106 and on to ribbon cable portion 116. Ribbon cable 102 has portion 116 into which electrode array 128 is integrally formed.

"Integrally formed" parts include those that are deposited, etched, cured, or formed at the same time as one another such that the result is that they are connected by a common material with one another, or as otherwise known in the art.

A "longitudinal" direction on a ribbon cable is a direction of longest measurements of the cable, or as otherwise known in the art. For example, a longitudinal direction in the figure is one running between the coil end and electrode end of the ribbon cable.

A "lateral" direction on a ribbon cable is a direction perpendicular to the longitudinal direction and within the plane of the ribbon cable, or as otherwise known in the art. For example, a lateral direction in the figure is one running from a far side of the cable (in the page) to a near side.

A "height" of a ribbon cable includes a direction of smallest dimensions, or as otherwise known in the art. For example, a height of the ribbon cable in the figure is one running vertically in the plane of the page.

A "ribbon cable" includes any cable having a flattened portion with conductors running side by side in the flattened portion, or as otherwise known in the art. A ribbon cable may be micro-fabricated or constructed using classical methods.

Before ribbon cable 102 has IC 126 attached, its electrodes will be electroplated in accordance with an embodiment. Afterwards, the cable can be used in surgical implants.

Figure 2:
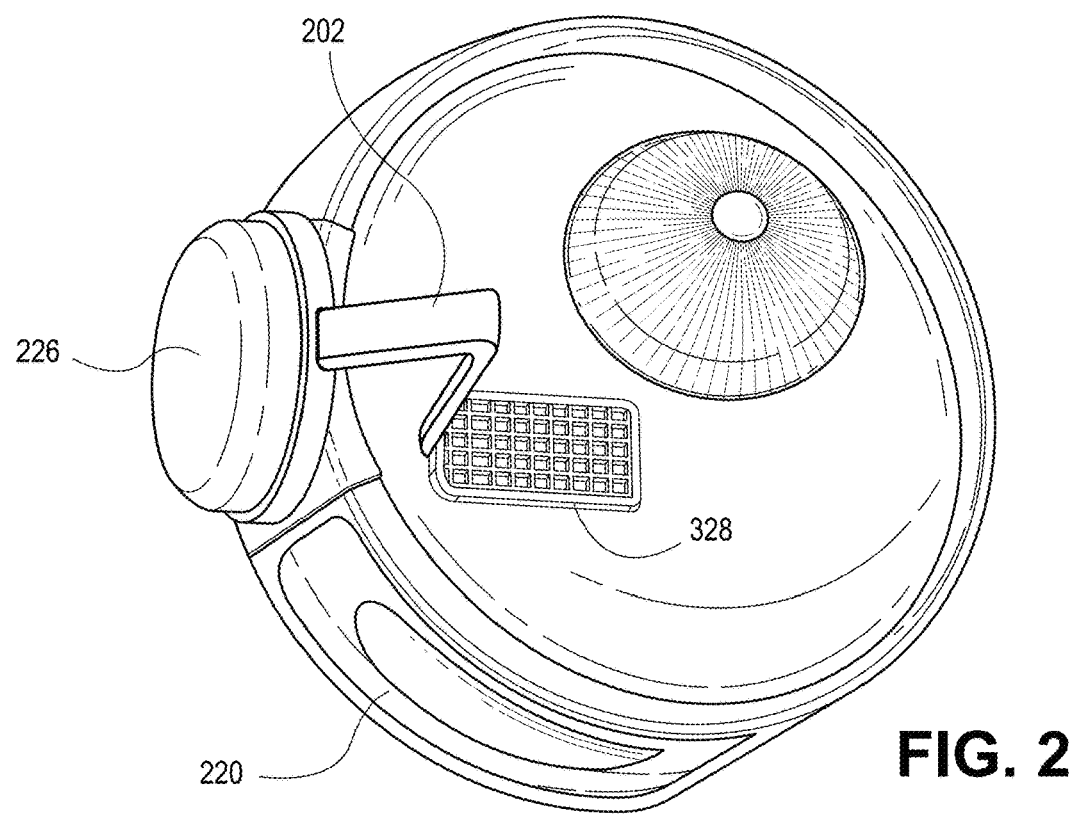
FIG. 2 is an illustration of a ribbon cable with electrodes surgically mated to an eyeball in accordance with an embodiment.

FIG. 2 is an illustration of a ribbon cable with electrodes surgically mated to an eyeball in accordance with an embodiment. Parylene ribbon cable 202 penetrates through the eye wall, allowing electrode array 228 to stimulate the eyeball's retina, specifically stimulating retinal ganglion cells within the eyeball. Application-specific integrated circuit (ASIC) 226 and receiver coil 220 are sutured between the conjunctiva and eyelid.

Figure 3:
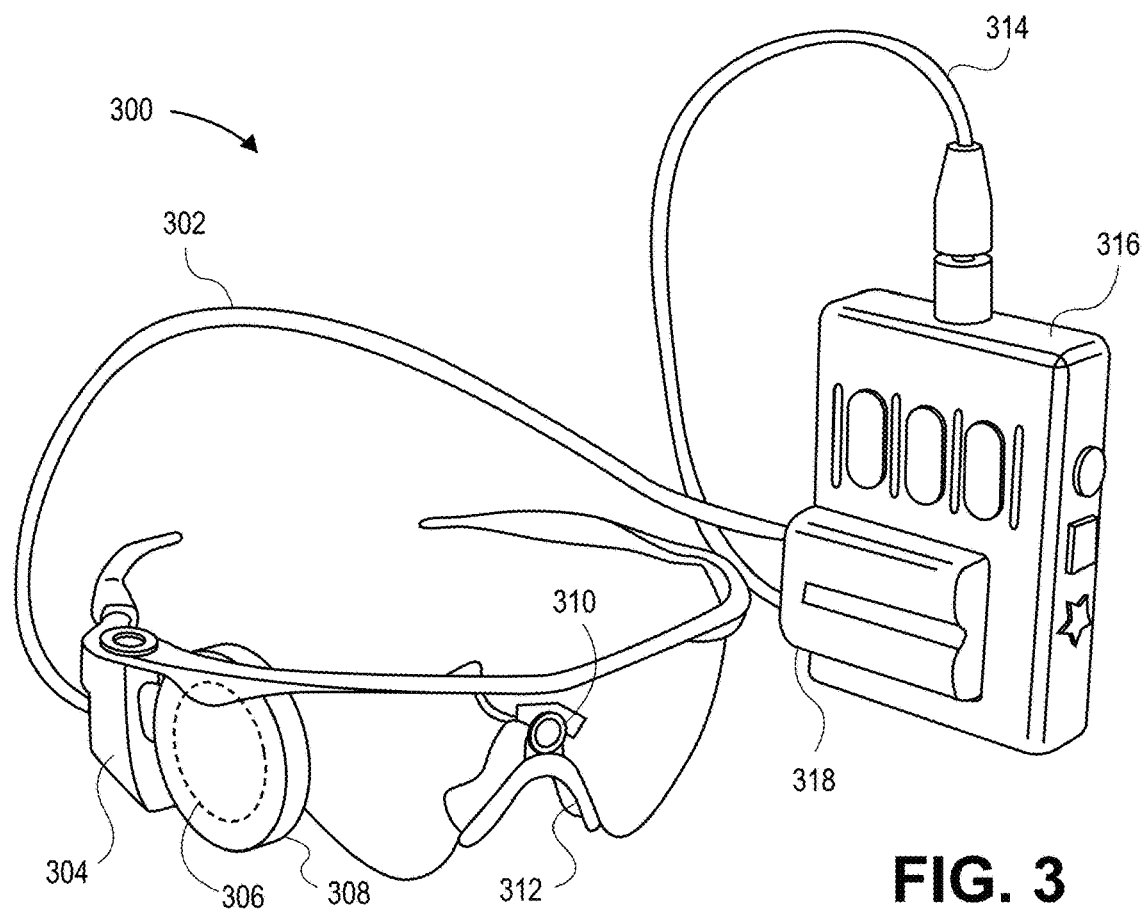
FIG. 3 illustrates a wearable transmitter assembly in accordance with an embodiment.

FIG. 3 illustrates a wearable transmitter assembly in accordance with an embodiment.

External unit 300 includes transmitter coil 306 housed in transmitter assembly 308. Transmitter assembly 308 is positioned to the side of a user's eye by glasses 312. Other positioning means besides glasses are envisioned.

Glasses 312 hold miniature camera 310 and video processor 304, which are connected by cable 302 to adaptor 318. Cable 314 connects another port of adaptor 318 to battery pack 316, which can be worn on a belt.

FIGS. 4A-4E illustrate a process flow for a group electroplating technique in accordance with an embodiment.

Figure 4A:
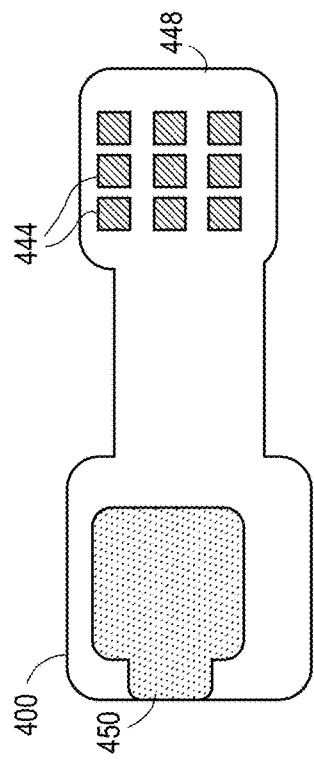
FIG. 4A illustrates deposition of metal traces and electrodes on a ribbon cable in accordance with an embodiment.

In FIG. 4A, a metal layer of titanium and/or gold are deposited on top of parylene to make workpiece 400. On the left side of workpiece 400 is a localized tap area 442 of conductive pads 440 that are suitable for connecting with one or more electrical components, such as IC chips, capacitors, resistors, inductors, transistors, and other components. They are connected by conductive metal to electrical leads 432, which run from first end 446 to opposing end 448 of the cable workpiece. Each electrical lead 432 is connected to a single electrode 444.

"Biocompatible" materials include those that have been determined by a government agency to avoid corrosion by bodily fluids for extended periods as well as be nontoxic. Titanium, gold, parylene, and polyimide are among the many biocompatible materials available for use in humans. For example, parylene has demonstrated bio-compatibility as a United States Pharmacopeial Convention (USP) Class VI biocompatible polymer.

Conductive pads 440 may be metal terminals, solder pads, connecting pads, or other conductive structures suitable for attaching electrical components. For IC chip components, the conductive pads may be configured to mate with a ball grid array (BGA), pin grid array (PGA), quad flat package (QFP) IC chips. Preferably, a conductive epoxy squeegee technique, combined with photo-patternable adhesives, achieves a high connection yield for high lean count IC chips with appropriate terminals.

A suitable conductive epoxy squeegee technique is described in Jay H. C. Chang, Ray Huang, and Y. C. Tai, "High density 256-channel chip integration with flexible parylene pocket," Proceeding of 16th International Conference on Solid-State Sensors, Actuators, and Microsystems (*Transducers* 2011), Beijing, China, 2011, pp. 378-381, which is hereby incorporated by reference.

Figure 4D:
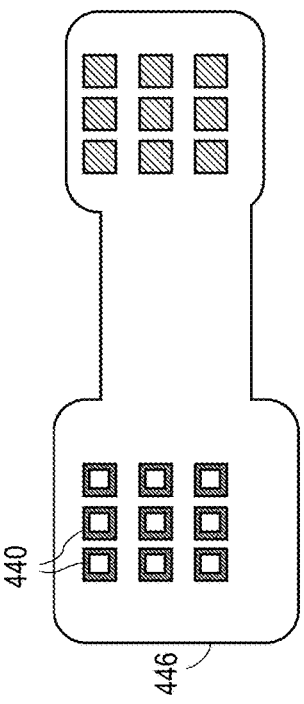
FIG. 4D illustrates the result of electroplating in accordance with an embodiment.
Figure 4B:
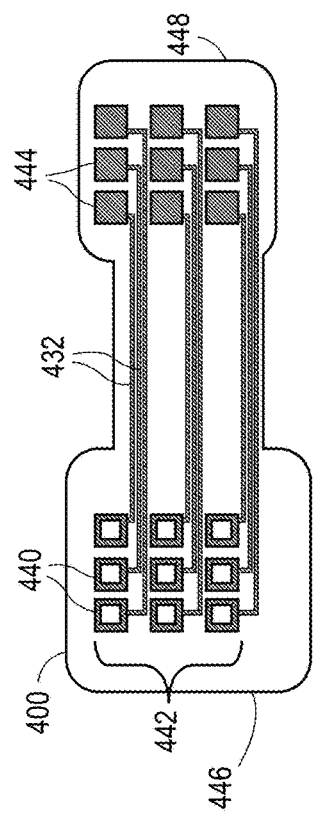
FIG. 4B illustrates embedding the traces and leaving the electrodes open in accordance with an embodiment.

In FIG. 4B, parylene is deposited on top of the metal layer sufficient to embed the electrical leads for most of the cable but keep portions of conductive pads 440 and electrodes 444 clear.

Figure 4E:
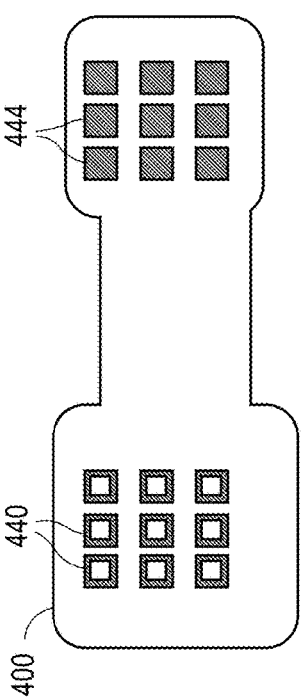
FIG. 4E illustrates removing the conductive sheet in accordance with an embodiment.
Figure 4C:
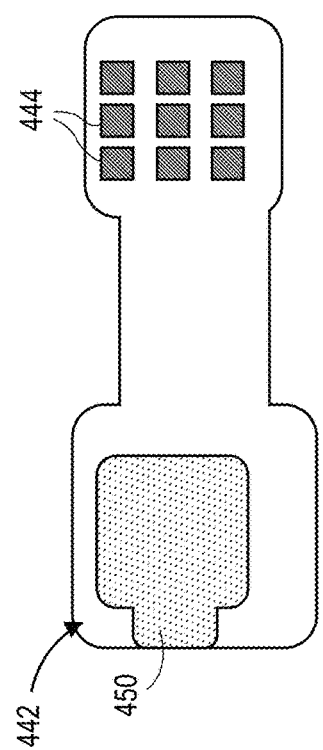
FIG. 4C illustrates depositing a continuous sheet of conductive material in accordance with an embodiment.

In FIG. 4C, aluminum coating 450 is applied by thermal evaporation to conductive pads 440 in localized tap area 442 such that leads 432 (FIG. 4A) and electrodes 444 are electrically shorted together through conductive aluminum coating 450.

In FIG. 4D, platinum black is electroplated over exposed electrodes 444 at end 448 using a power supply connected with conductive metal sheet 450.

In FIG. 4E, conductive aluminum tab 450 has been removed from end 446 to expose conductive pads 440.

FIGS. 5A-5M illustrate micro-fabrication steps to create a ribbon cable with electroplated electrodes.

Figures 5A, 5B, 5C, 5D, 5E, 5F, 5G, 5H, 5I, 5J, 5K, 5L, 5M:
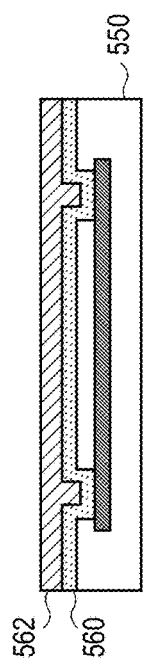
FIG. 5A illustrates depositing parylene in accordance with an embodiment.
FIG. 5B illustrates depositing metal over the parylene of FIG. 5A.
FIG. 5C illustrates depositing parylene over the metal of FIG. 5B.
FIG. 5D illustrates applying photoresist as a mask over the workpiece of FIG. 5C to open electrodes in accordance with an embodiment.
FIG. 5E illustrates opening the electrodes of FIG. 5D.
FIG. 5F illustrates the result of removing photoresist of FIG. 5E.
FIG. 5G illustrates depositing aluminum over the workpiece of FIG. 5F.
FIG. 5H illustrates applying photoresist as a mask to pattern the aluminum of FIG. 5G.
FIG. 5I illustrates the results of patterning the aluminum of FIG. 5H.
FIG. 5J illustrates removing all but a tab of aluminum from the workpiece of FIG. 5I.
FIG. 5K illustrates the result of removing photoresist from the workpiece of FIG. 5K.
FIG. 5L illustrates applying voltage to the tab of aluminum to electroplate the workpiece of FIG. 5L.
FIG. 5M illustrates the result of removing the tab from the workpiece of FIG. 5L.

FIG. 5A shows a bottom layer of parylene polymer being deposited on a flat surface of silicone to create the beginning of workpiece 550.

FIG. 5B shows a metal layer 552 of traces, conductive pads, electrodes, and other features deposited onto the parylene. This may occur in several steps of depositing metal, photomasking and exposing, and etching.

FIG. 5C shows parylene layer 554 deposited over metal layer 552 to encapsulate and embed metal layer 552.

FIG. 5D shows photoresist layer 556 patterned on top of workpiece 550. The pattern for photoresist layer 556 includes open areas to the metal layer for conductive pads and electrodes.

FIG. 5E shows the results of dissolving or etching away parylene in the unprotected areas of parylene not covered by developed photoresist. The parylene in the uncovered areas is removed all of the way down to metal layer 552 to create openings 558 to the metal conductive pads and electrodes of workpiece 550.

FIG. 5F shows the results of removing the photoresist layer from the previous operation.

FIG. 5G shows the deposition of aluminum layer 560 by thermal evaporation over workpiece 550. This layer will become the conductive tab that shorts all of the conductive tabs together. Other metals, such as titanium, can also be used. Preferably, the electrically conductive material for the tab should be able to be cleanly removed later by etching, peeling, or other methods without destroying the conductive pads or insulative parylene below.

FIG. 5H shows photoresist layer 562 being applied over aluminum layer 560.

FIG. 5I shows photoresist layer 562 being masked, exposed, and washed to reveal portions of aluminum layer 560 that will be removed.

FIG. 5J shows the remaining tab portion of aluminum layer 560 under photoresist layer 562, minus the portion of aluminum layer 560 that covered other portions of the cable. The remaining portion 560 shorts all of the conductive pads (and electrodes) together as a conductive tab.

In some embodiments, a conductive tape is adhered to the end of the cable with the conductive pads that shorts together the conductive pads. Using conductive tape can avoid the metal deposition, masking, etc. operations shown in FIGS. 5G-5I. However, conductive tape may not bond properly to each and every conductive pad, which can be 100 µm in width and 100 µm from one another and slightly recessed from the cable surface.

FIG. 5K shows workpiece 550 and aluminum layer 560 after the photoresist layer is removed.

FIG. 5L shows workpiece 550 being electroplated using a single connection clip 564 to aluminum tab 560 for an electroplating voltage source. With the opposing end of the cable—with the electrodes—immersed in an electrolyte solution, the electrodes are all plated with plating material 566.

FIG. 5M shows workpiece 550 with the voltage source and aluminum tab removed, leaving ribbon cable 550 with electrodes each plated with plating material 566. The aluminum tab can be dissolved away by etching solution.

If a conductive tape is used for the tab, it can be peeled way. Aluminum, gold, platinum, silver, titanium, and other metals and non-metals may be suitable conductive materials for temporarily shorting the conductive pads together.

The array of conductive pads can be in a regularly spaced array or be randomly or non-regularly spaced. The array can be square, rectangular, circular, or other shapes. The array can be planar, or it can vary in height.

Figure 6:
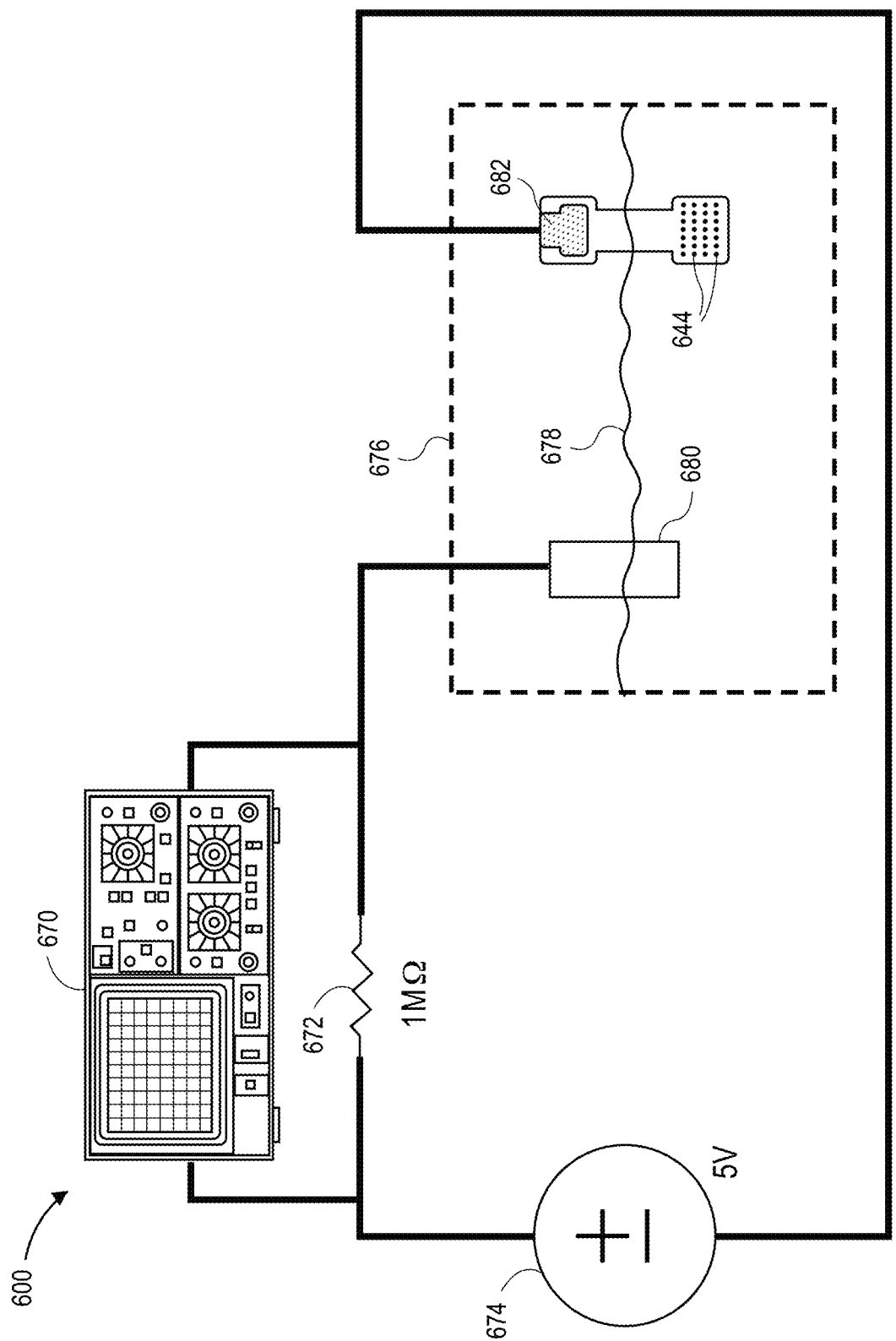
FIG. 6 diagrams an electroplating system in accordance with an embodiment.

FIG. 6 diagrams an electroplating system in accordance with an embodiment. In system 600, voltage source pulse generator 674 is connected in series with 1 MΩ resistor 672 to give a relatively stable current during plating. Oscilloscope 670 monitors the voltage across the resistor, from which the plating current can be derived.

Vessel 676 holds electrolyte solution 678 into which platinum counter electrode 680 and the electrode end 682 of a ribbon cable are immersed on opposite ends. The positive terminal of power supply 674 is connected to counter electrode 680. The negative terminal of power supply 674 is connected in one location at conductive sheet 682, which is electrically connected to each and every electrode 644 through the ribbon cable. A 5 volt potential is applied in the exemplary embodiment.

Figure 7:
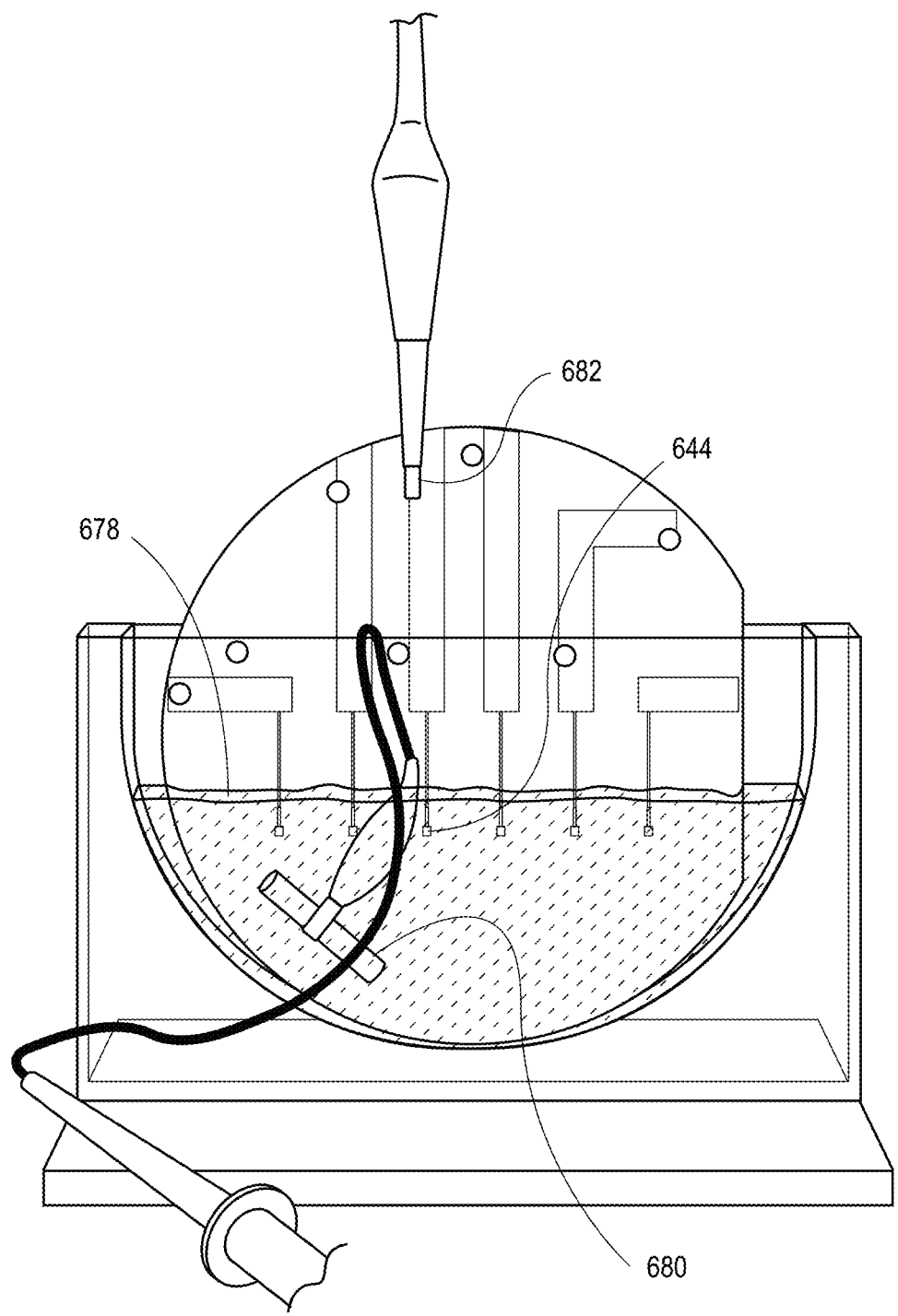
FIG. 7 illustrates a laboratory electroplating system in accordance with an embodiment.

FIG. 7 illustrates an electroplating system in accordance with an embodiment. In the laboratory setup, an alligator clip is for the negative voltage is connected with conductive tab 682 of a ribbon cable, which connects the negative voltage to electrodes 644. Electrodes 644 are immersed in electrolyte solution 678. Also immersed in electrolyte solution 678 is platinum counter electrode 680, which is attached by an alligator clip to the positive voltage of the power supply.

Samples with 16-electrode arrays are shown, each array with electrode sizes of 66 µm×66 µm. A custom holder is designed for samples to be electroplated on a silicon wafer, which is mechanically reliable.

Figure 8:
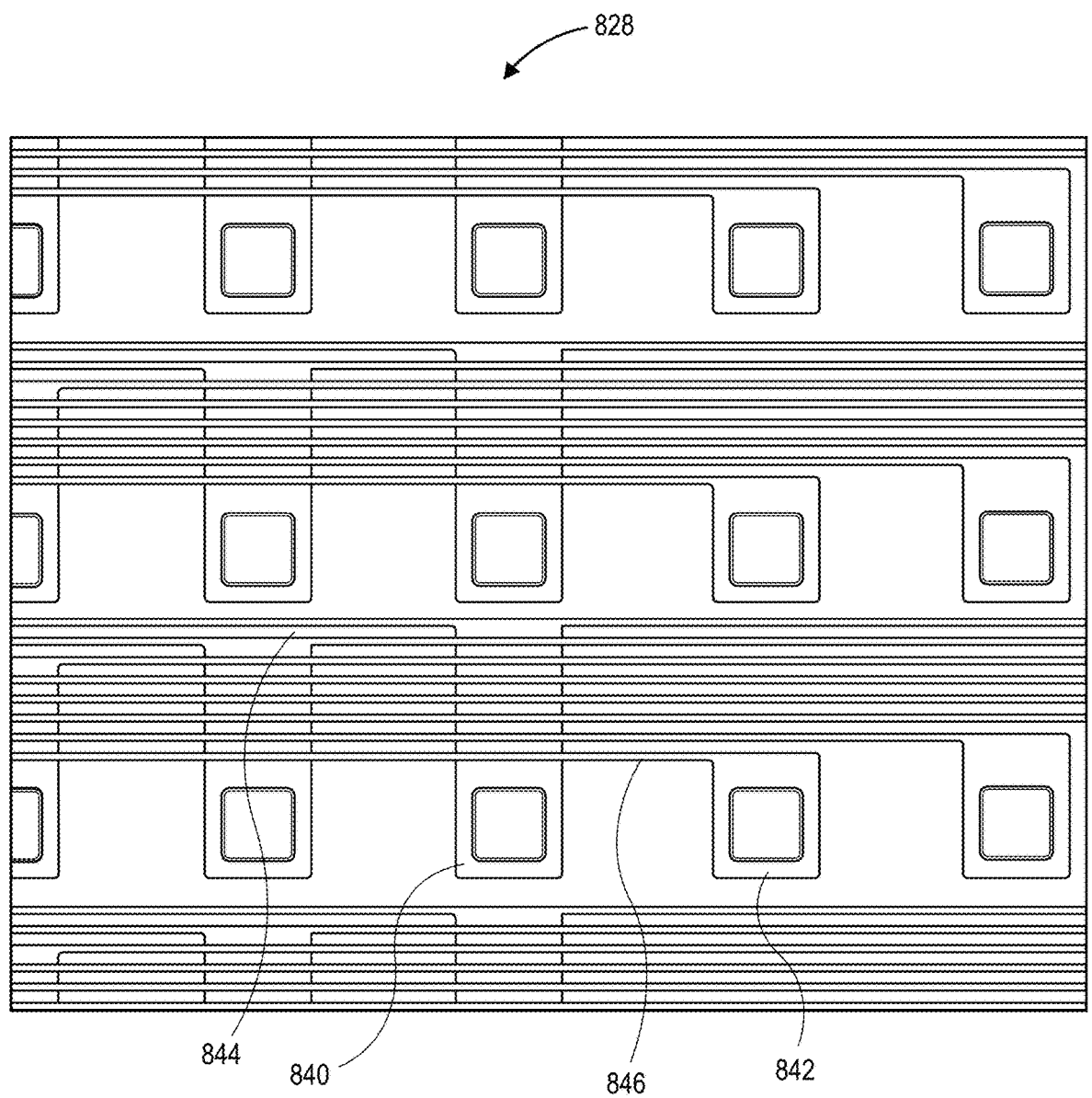
FIG. 8 illustrates a close-up view of a dual metal layer electrode array in accordance with an embodiment.

FIG. 8 illustrates a close-up view of a dual metal layer electrode array in accordance with an embodiment. A dual metal layer electrode array can pack more lines for electrodes in a smaller amount of area than a single metal layer. In electrode array 828, conductive pad 840 is connected through a via to bottom layer traces 844, which run underneath top layer traces 846. Conductive pad 842 is connected to top layer trace 846. Each of the electrodes can be plated in accordance with the methods described.

Figures 9A, 9B:
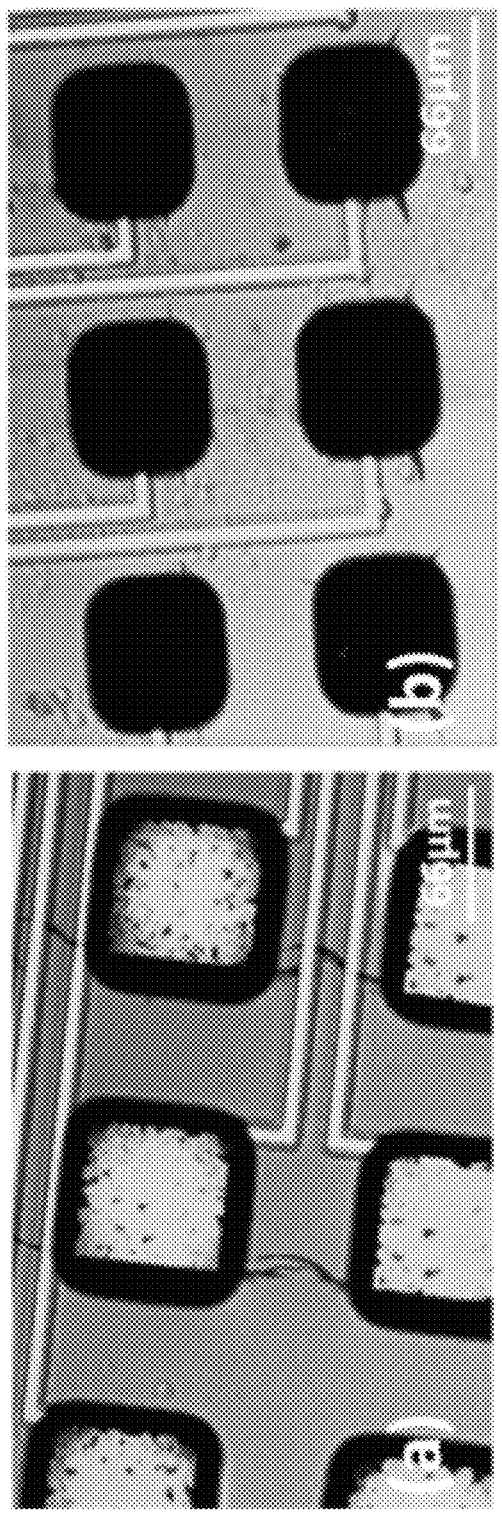
FIG. 9A is an image of electrodes before plating.
FIG. 9B is an image of electrodes after plating in accordance with an embodiment.

FIG. 9A is an image of electrodes before plating. The dark regions around each square electrode are an artifact of the micrograph; the dark regions around each square are simply parylene that is slanted down in a bezel to meet the square metal electrode.

FIG. 9B is an image of electrodes after plating in accordance with an embodiment. In this micrograph, the electrodes have been plated with platinum black, which appears completely black in the image.

Figure 10:
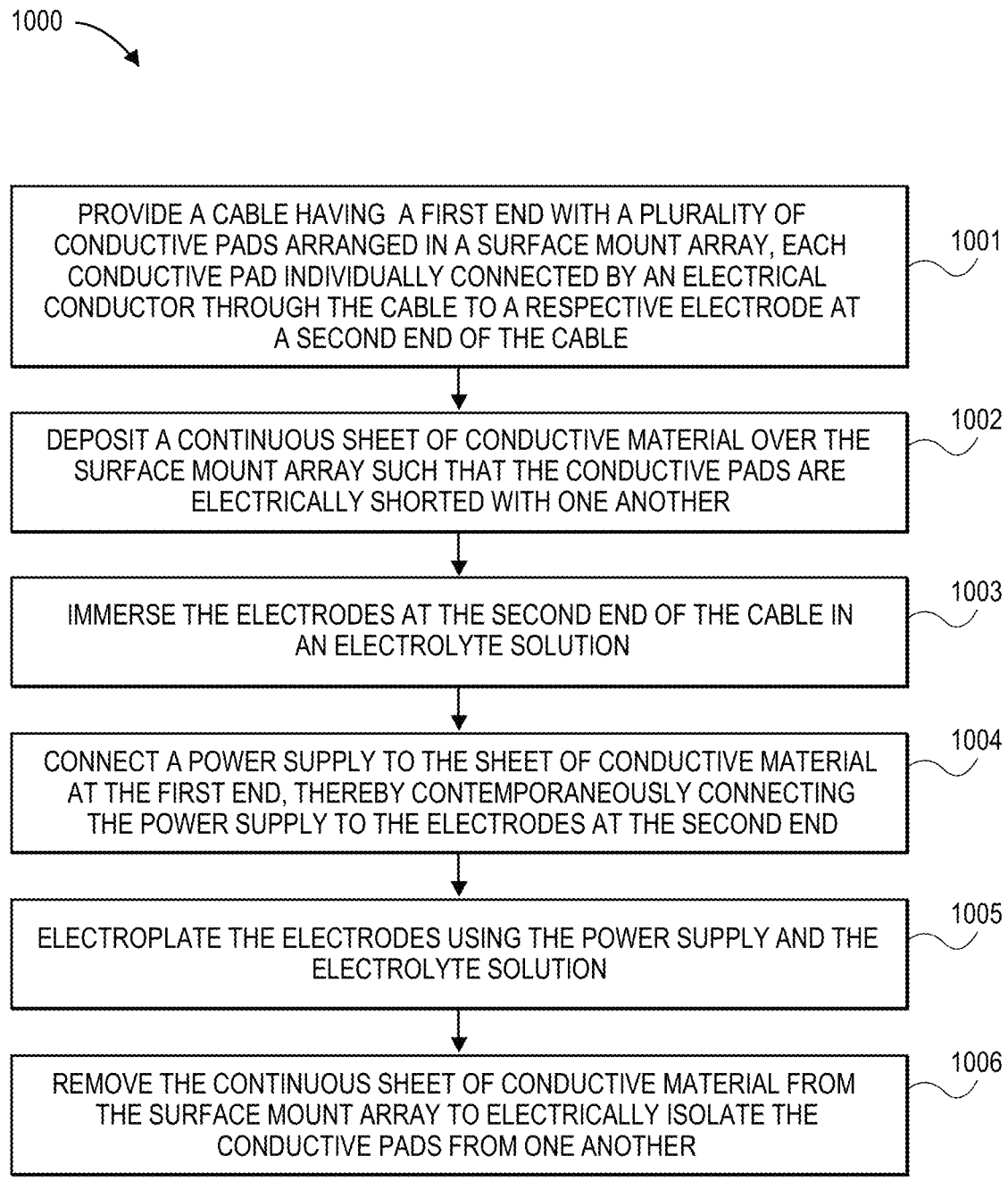
FIG. 10 is a flowchart of a process in accordance with an embodiment.

FIG. 10 is a flowchart of process 1000 in accordance with an embodiment. In operation 1001, a cable is provided having a first end with a plurality of conductive pads arranged in a surface mount array, each conductive pad individually connected by an electrical conductor through the cable to a respective electrode at a second end of the cable. In operation 1002, a continuous sheet of conductive material is deposited over the surface mount array such that the conductive pads are electrically shorted with one another. In operation 1003, the electrodes at the second end of the cable are immersed in an electrolyte solution. In operation 1004, a power supply is connected to the sheet of conductive material at the first end, thereby contemporaneously connecting the power supply to the electrodes at the second end of the ribbon cable. In operation 1005, the electrodes are electroplated using the power supply and the electrolyte solution. In operation 1006, the continuous sheet of conductive material is removed from the surface mount array to electrically isolate the conductive pads from one another.

Figure 11:
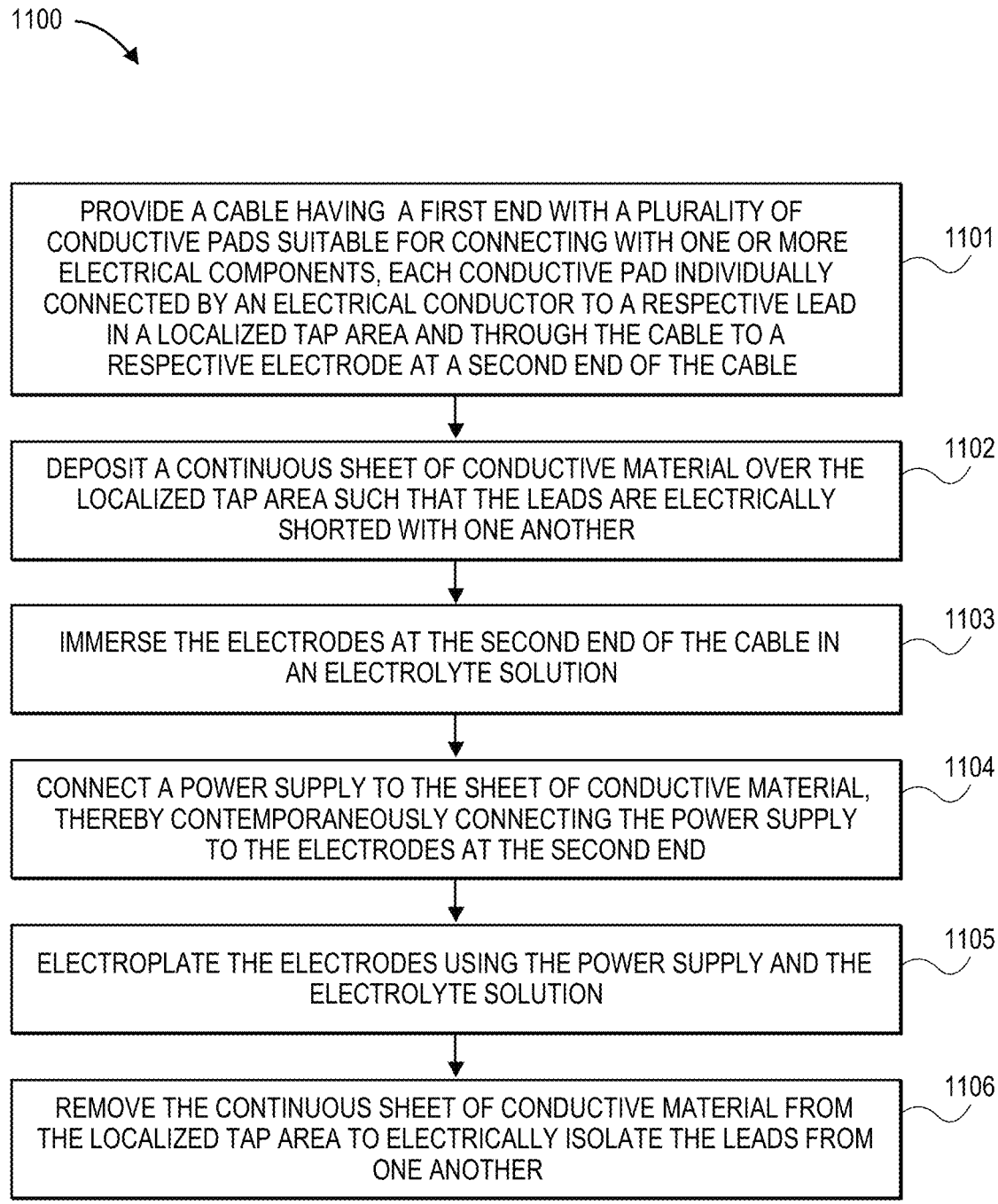
FIG. 11 is a flowchart of a process in accordance with an embodiment.

FIG. 11 is a flowchart of process 1100 in accordance with an embodiment. In operation 1101, a cable having a first end with a plurality of conductive pads suitable for connecting with one or more electrical components, each conductive pad individually connected by an electrical conductor to a respective lead in a localized tap area and through the cable to a respective electrode at a second end of the cable. In operation 1102, a continuous sheet of conductive material is deposited over the localized tap area such that the leads are electrically shorted with one another. In operation 1103, the electrodes are immersed at the second end of the cable in an electrolyte solution. In operation 1104, a power supply is connected to the sheet of conductive material, thereby contemporaneously connecting the power supply to the electrodes at the second end. In operation 1105, the electrodes are electroplated using the power supply and the electrolyte solution. In operation 1106, the continuous sheet of conductive material is removed from the localized tap area to electrically isolate the leads from one another.

The invention has been described with reference to various specific and illustrative embodiments. However, it should be understood that many variations and modifications may be made while remaining within the spirit and scope of the following claims.

What is claimed is:

1. A method of electroplating electrodes on a cable, the method comprising:
providing a cable having a first end with a plurality of recessed conductive pads arranged in recesses of a surface mount array, each recessed conductive pad arranged in one of the recesses of the surface mount array and individually connected by an electrical conductor through the cable to a respective recessed electrode at a second end of the cable, the recesses of the surface mount array being below a top surface of the surface mount array;
depositing, using at least one of thermal evaporation, sputtering deposition, or chemical vapor deposition, a continuous sheet of conductive material over the top surface of the surface mount array and into the recesses of the surface mount array such that the recessed conductive pads are electrically shorted with one another, the continuous sheet of conductive material having a tab portion that is over the top surface of the surface mount array;
immersing the recessed electrodes at the second end of the cable in an electrolyte solution;
connecting a power supply to the tab portion of the conductive material at the first end, thereby contemporaneously connecting the power supply to the recessed electrodes at the second end;
electroplating the recessed electrodes at the second end with a metal such that the metal covers the electrodes and fills recesses corresponding to the recessed electrodes to a top surface of a surrounding insulator using the power supply and the electrolyte solution; and
removing the continuous sheet of conductive material by chemically etching the tab portion from the surface mount array to electrically isolate the recessed conductive pads from one another.

2. The method of claim 1 wherein the recessed conductive pads in the surface mount array are each less than 100 μm in width and less than 100 μm from one another.

3. The method of claim 1 wherein the metal includes platinum black.

4. The method of claim 1 further comprising:
depositing the continuous sheet of conductive material over the first end of the cable such that the continuous sheet of conductive material is larger than the surface mount array;
applying photoresist to the first end of the cable;
exposing a photomask to the first end of the cable; and
removing excess conductive material to leave the continuous sheet of conductive material over the surface mount array.

5. The method of claim 1 wherein the continuous sheet comprises a material selected from the group consisting of aluminum, gold, platinum, silver, and titanium.

6. The method of claim 1 wherein the metal is selected from the group consisting of pure platinum, gold, and iridium.

7. The method of claim 1 wherein the surface mount array is square or rectangular.

8. The method of claim 1 wherein the surface mount array is circular.

9. The method of claim 1 further comprising:
mounting an integrated circuit (IC) chip or IC socket to the surface mount array of the cable.

10. The method of claim 9 wherein the IC chip comprises a plurality of metal pads in a two-dimensional array on a bottom of the IC chip, each metal pad of the IC chip connected to the surface mount array of the cable by conductive epoxy.

11. A method of electroplating electrodes on a cable, the method comprising:
providing a cable having a first end with a plurality of recessed conductive pads suitable for connecting with one or more electrical components, each recessed conductive pad arranged in one of recesses of a localized tap area and individually connected by an electrical conductor to a respective lead in the localized tap area and through the cable to a respective recessed electrode at a second end of the cable, wherein at least one of the plurality of recessed conductive pads is arranged in a recess of the localized tap area;
depositing, using at least one of thermal evaporation, sputtering deposition, or chemical vapor deposition, a continuous sheet of conductive material over the top surface of the localized tap area and into the recessed conductive pads and the recess such that the leads are electrically shorted with one another, the continuous sheet of conductive material having a tab portion that is over the top surface of the localized tap area;
immersing the recessed electrodes at the second end of the cable in an electrolyte solution;
connecting a power supply to the tab portion of the conductive material, thereby contemporaneously connecting the power supply to the recessed electrodes at the second end;
electroplating the recessed electrodes at the second end with a metal such that the metal covers the electrodes and fills recesses corresponding to the recessed electrodes to a top surface of a surrounding insulator using the power supply and the electrolyte solution; and
removing the continuous sheet of conductive material by chemically etching the tab portion from the localized tap area to electrically isolate the leads from one another.

12. The method of claim 11 further comprising:
depositing the continuous sheet of conductive material over the localized tap area such that the continuous sheet of conductive material is larger than the localized tap area;
applying photoresist to the first end of the cable;
exposing a photomask to the first end of the cable; and
removing excess conductive material to leave the continuous sheet of conductive material over the localized tap area.

13. The method of claim 11 further comprising:
mounting an integrated circuit (IC) chip or IC socket to the localized tap area of the cable.

14. The method of claim 13 wherein the IC chip comprises a plurality of metal pads in a two-dimensional array on a bottom of the IC chip, each metal pad of the IC chip connected to the localized tap area of the cable by conductive epoxy.

15. The method of claim 1 wherein the continuous sheet is a rounded corner rectangle.

16. The method of claim 11 wherein the continuous sheet is a rounded corner rectangle.

17. The method of claim 1 wherein the connecting is performed using a single connection clip.

18. The method of claim 11 wherein the connecting is performed using a single connection clip.

19. The method of claim 1 wherein the tab portion ends at an outer edge of the top surface.

20. The method of claim 11 wherein the tab portion ends at an outer edge of the top surface.

* * * * *